(12) United States Patent
Therkelsen et al.

(10) Patent No.: US 7,867,207 B2
(45) Date of Patent: Jan. 11, 2011

(54) COUPLING ASSEMBLY

(75) Inventors: Henning Therkelsen, Aarhus N (DK); Holm Tina Soerensen, Holstebro (DK); Ole Madsboel, Braband (DK); Laesoe Ingrid Fink, Lynge (DK)

(73) Assignee: Coloplast A/S, Humlebaek (DK)

( * ) Notice: Subject to any disclaimer, the term of this patent is extended or adjusted under 35 U.S.C. 154(b) by 301 days.

(21) Appl. No.: 12/083,961

(22) PCT Filed: Nov. 23, 2006

(86) PCT No.: PCT/DK2006/000655
§ 371 (c)(1),
(2), (4) Date: Apr. 23, 2008

(87) PCT Pub. No.: WO2007/059775
PCT Pub. Date: May 31, 2007

(65) Prior Publication Data
US 2009/0163886 A1     Jun. 25, 2009

(30) Foreign Application Priority Data
Nov. 24, 2005   (DK) ............................. 2005 01658

(51) Int. Cl.
| A61M 31/00 | (2006.01) |
| A61F 5/44 | (2006.01) |
| F16B 7/06 | (2006.01) |
| F16B 7/10 | (2006.01) |
| F16B 7/04 | (2006.01) |
| F16B 21/09 | (2006.01) |
| F16G 11/12 | (2006.01) |
| F16C 11/00 | (2006.01) |
| F16K 31/60 | (2006.01) |
| F16D 1/00 | (2006.01) |

(52) U.S. Cl. ............ 604/342; 604/277; 604/278; 604/332; 604/337; 604/341; 604/343; 604/344; 604/355; 403/43; 403/52; 403/202; 403/217; 403/315; 403/345; 403/410

(58) Field of Classification Search ............... 604/342, 604/277, 278, 332, 337, 341, 343, 344, 355
See application file for complete search history.

(56) References Cited

U.S. PATENT DOCUMENTS

| 3,653,670 | A | * | 4/1972 | Sifri et al. | ................. 277/438 |
| 4,050,461 | A | * | 9/1977 | Ruby | ........................ 604/277 |
| 4,174,846 | A | * | 11/1979 | Scott | ......................... 277/556 |
| 4,618,154 | A | * | 10/1986 | Freudenthal | ............... 277/556 |
| 4,816,023 | A | * | 3/1989 | Freeman | ..................... 604/339 |
| 4,973,324 | A | * | 11/1990 | Steer | ......................... 604/342 |
| 5,178,615 | A | * | 1/1993 | Steer et al. | ................. 604/338 |
| 5,322,523 | A | * | 6/1994 | Olsen | ........................ 604/338 |
| 5,364,379 | A | * | 11/1994 | Ozenne et al. | ............. 604/342 |
| 5,496,297 | A | * | 3/1996 | Olsen | ........................ 604/339 |

(Continued)

Primary Examiner—Leslie R Deak
Assistant Examiner—Adam Marcetich
(74) Attorney, Agent, or Firm—Coloplast Corp., Coloplast A/S; Daniel G. Chapik; Nicholas R. Baumann

(57) ABSTRACT

The present invention relates to a coupling assembly such as a coupling assembly for coupling an ostomy bag to a base plate, said base plate being adhered around a stoma. The present invention especially relates to a coupling assembly comprising a first, second and third coupling part, which are coupled together to form a coupling assembly.

14 Claims, 7 Drawing Sheets

U.S. PATENT DOCUMENTS 5,709,674 A * 1/1998 Steer .......................... 604/342
5,830,200 A * 11/1998 Steer et al. .................. 604/338
6,802,831 B2 * 10/2004 Plass et al. .................. 604/332

* cited by examiner

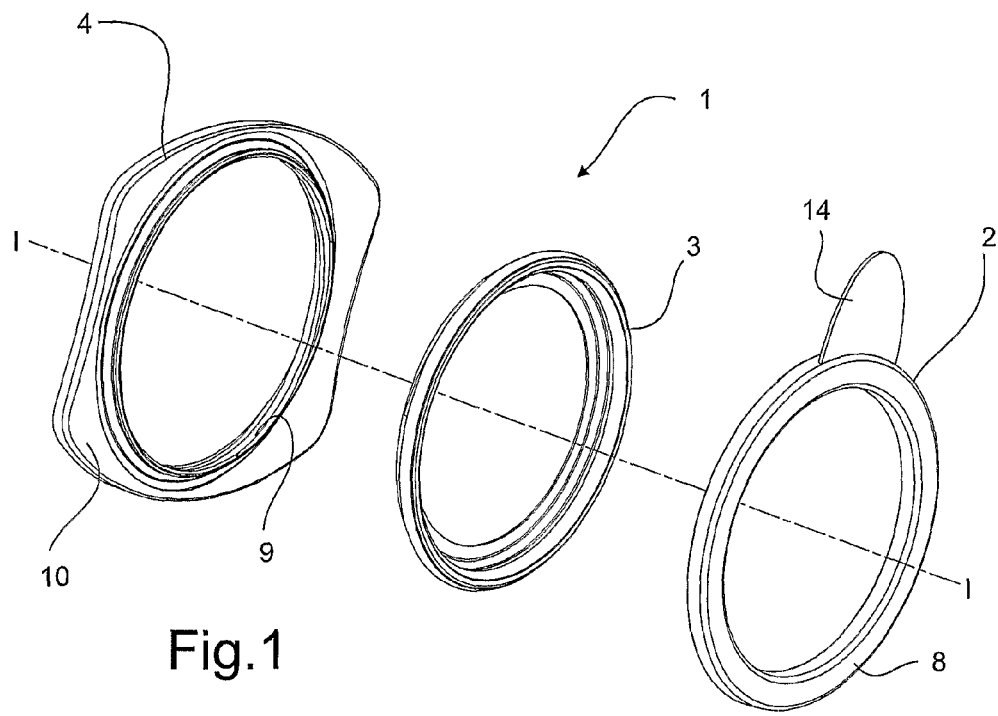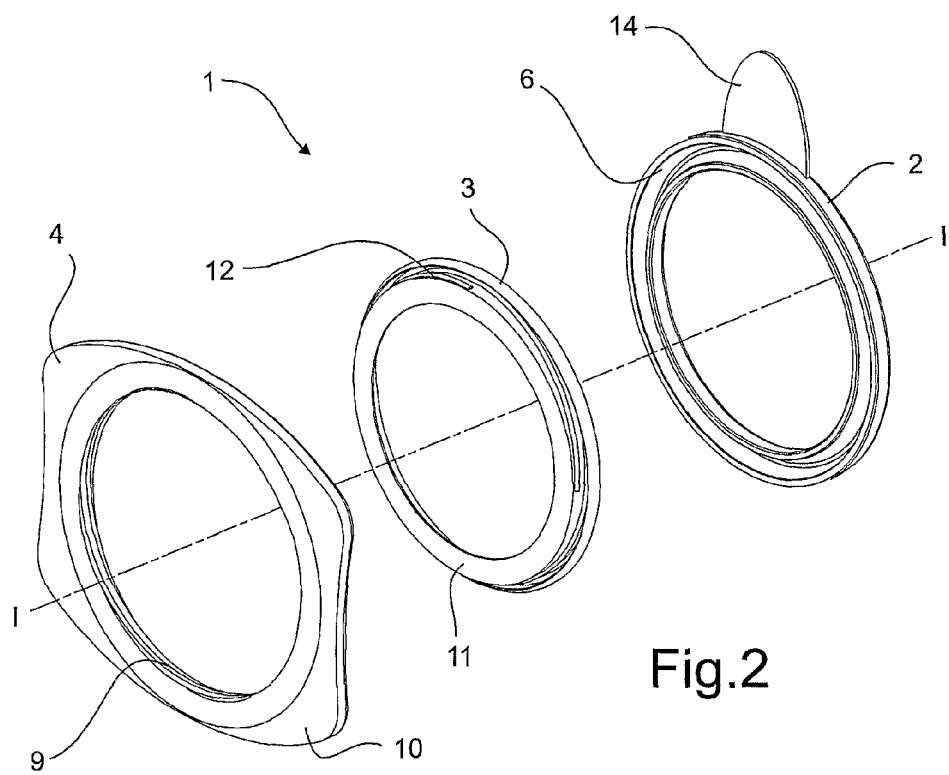

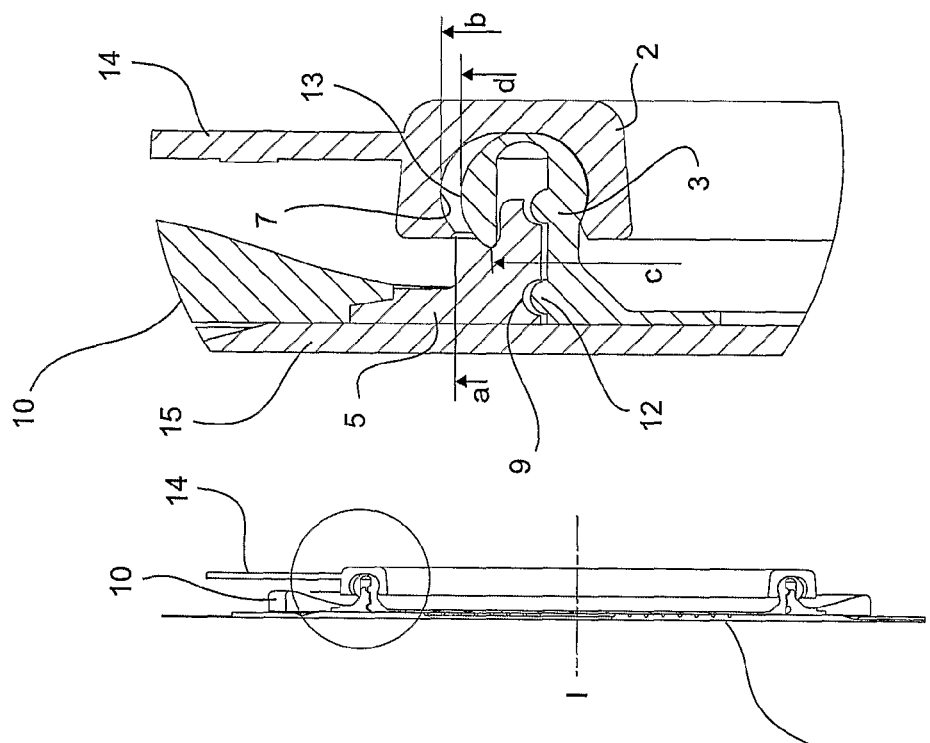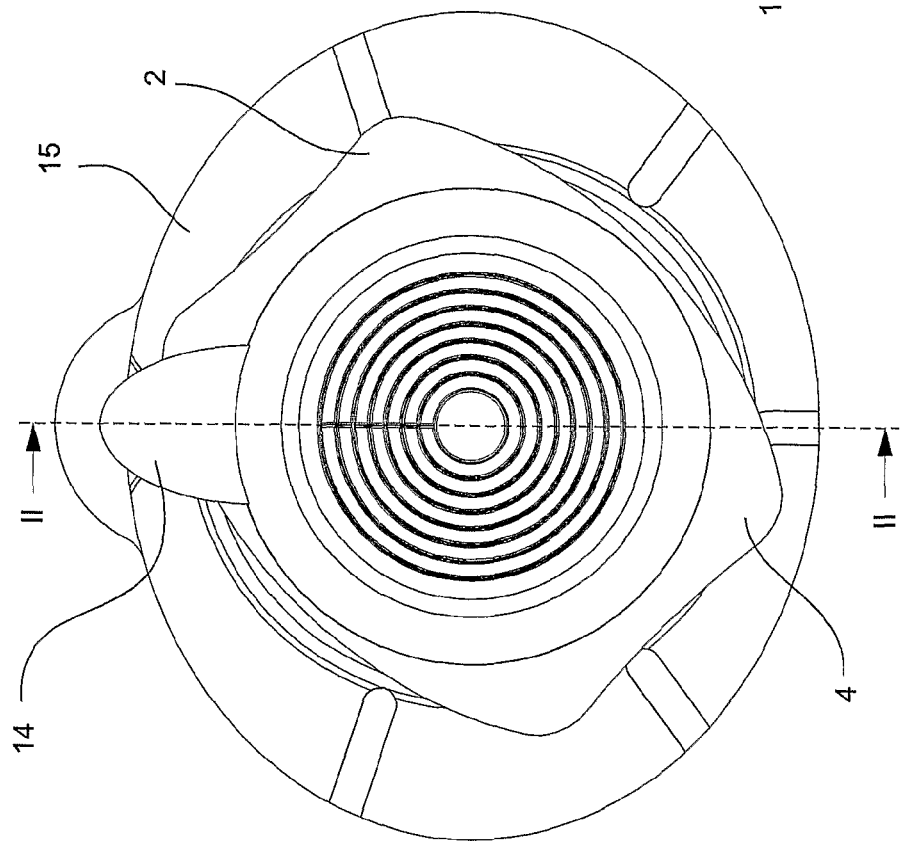

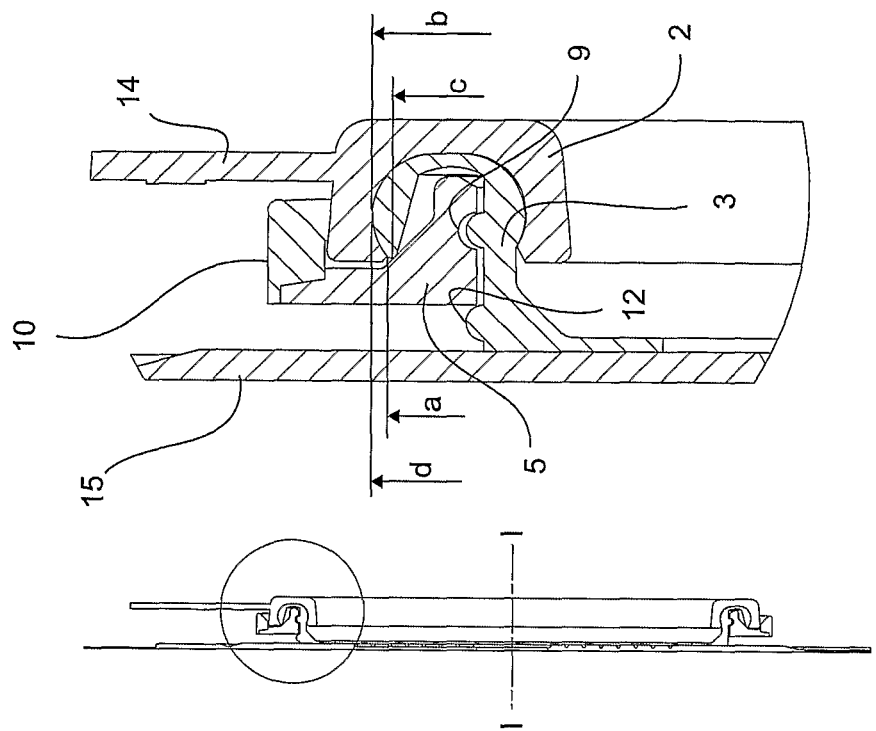
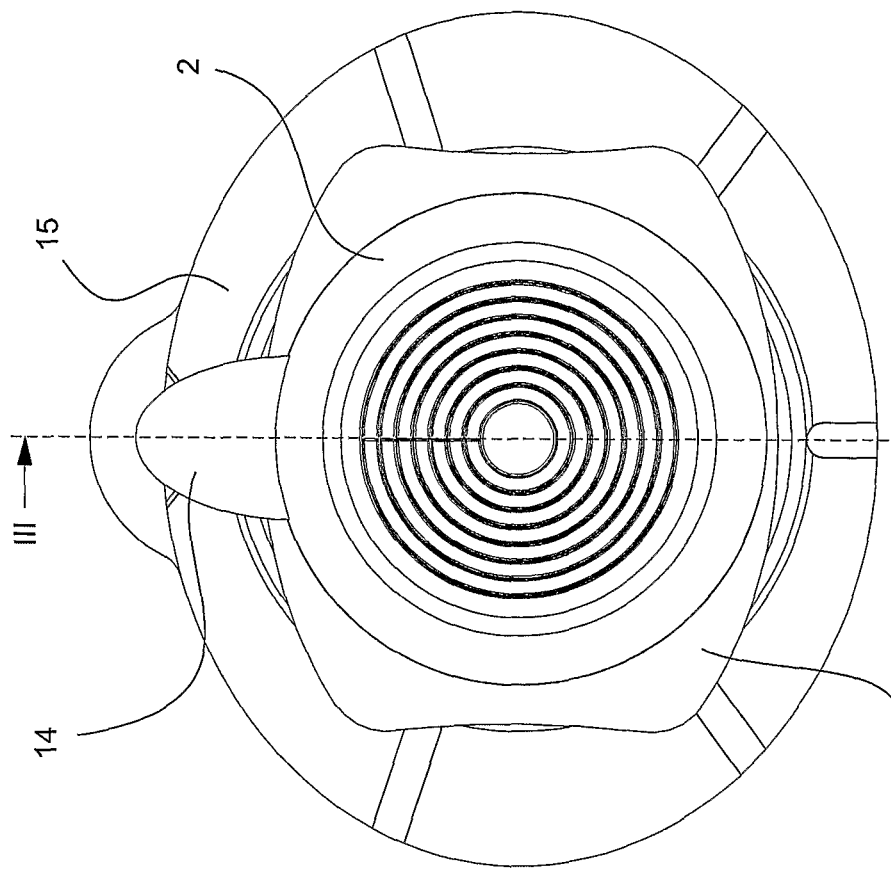

COUPLING ASSEMBLY

This is a national stage of PCT/DK06/000655 filed Nov. 23, 2006 and published in English.

FIELD OF THE INVENTION

The present invention relates to a coupling assembly, such as a coupling assembly for coupling an ostomy bag to a base plate, said base plate being adhered to an area around a stoma.

BACKGROUND

Ostomy coupling arrangements are used to connect so called two-piece ostomy bags. These two-piece ostomy bags comprises an ostomy bag for receiving stomal discharge, the ostomy bag having a coupling part which is adapted to couple with a coupling part on a base plate which is adhered to the skin of the user in an area around the stoma.

In this way the ostomy bag can be changed after use without having to change the base plate each time.

Many different types of coupling arrangements for securing an ostomy bag to a base plate are known all trying to fulfill different demands for the coupling between the base plate and the ostomy bag. Such demands are for example that the couplings are tight and secure so that no stoma discharge is leaked, that the coupling is discreet so that the ostomy bag can be carried beneath ordinary clothes and that the coupling is easy to operate.

In U.S. Pat. No. 4,846,798 a two-piece ostomy bag is proposed having two coupling parts, one of the parts being intended for fixation on the body of the user and the other part including a collecting pocket for collecting body fluids and/or waste. The bag-side coupling part is fixated on the collecting bag. The connection between the body-side part and the bag-side part of the coupling is done through a threaded hub. The body-side coupling part has an annular protruding rim provided with a thread on the outer surface of the rim for engagement with a corresponding thread on the bag-side coupling part.

EP 0 334 489 discloses an ostomy coupling including a first channel shaped element for attaching to an ostomy bag and a second element for attaching to a pad of medical grade adhesive, each of these elements surrounding a stomal orifice, in which the second element comprises a first part for attaching to the pad and a second part which is axially slidable relative to the first part for coupling the elements together and which second part has a radially outer external flange under which the fingers can be placed when joining the elements to substantially prevent the application of pressure to the peristomal area.

SUMMARY

Among others it is an aspect of the present invention to provide an improved coupling assembly which is safe to wear and does not accidentally uncouple.

Another aspect according to the invention is a coupling assembly which is easy to couple and uncouple.

Another aspect according to the invention is a coupling assembly which is discrete and comfortable to wear.

Another aspect according to the invention is a coupling assembly that provides a tight and secure seal.

Another aspect according to the invention is a coupling assembly, which makes it easy for the user to establish that the coupling is correctly mounted and thus provides a safe and tight seal.

The present invention relates to a coupling assembly comprising a first, second and third coupling element for coupling a first and second part to each other in an axial direction, wherein the first coupling element comprises a first engagement area, extending between a first inner radius and a first outer radius, the second coupling element comprises a second engagement area, extending between a second inner radius and a second outer radius, the second engagement area being radially displaceable between an engagement position, where the second outer radius is larger than the first inner radius, and a disengagement position, where the second outer radius is smaller than the first inner radius, the third coupling element comprising a locking member and being axially displaceable in relation to the second coupling element between a locking position and an unlocking position, and wherein the second engagement area is secured in its engagement position when the locking member is in its locking position.

The present invention is described by way of example using an ostomy coupling as an example. However, the scope of the invention is by no means limited by this example. The skilled person will appreciate the invention in other applications.

In this example the second and third coupling element is placed on a body-side coupling part, while the first coupling element is placed on a bag-side coupling part. However, this particular embodiment is only an example of the invention, and the skilled person will appreciate other embodiments of the invention, e.g. where the first coupling element is placed on the body-side coupling part, and the second and third coupling elements are placed on the bag-side coupling part.

The term "radially displaceable" is in this application used to describe that the second coupling element can be displaced radially in relation to a central axis.

In one embodiment of the invention the coupling assembly is a coupling assembly for a two-piece ostomy bag including a body-side coupling part and a bag-side coupling part. The coupling assembly is particularly suitable for coupling a two-piece ostomy bag, as it provides a tight coupling and at the same time is easy to handle and can be worn discretely. In a preferred embodiment the inner surface of the second coupling element, which inner surface faces the stoma, is provided as an even and smooth surface, which is easy to clean. When changing a two-piece ostomy bag, the body side coupling part is often left on the skin of the user to be used again, while the bag-side coupling part is disposed off along with the used ostomy bag. Thus, easy cleaning of the reusable body-side coupling part is important for the user in order to minimize cleaning time, and thus easy cleaning provides convenience for the user. A body-coupling part, which is hard to clean due to e.g. uneven surfaces in the form of ridges, edges, notches or the like, will often result in the risk of odour problems and thus decrease the users perceived comfort. An easy to clean body-side coupling part is more hygienic, when cleaned properly, since stomal discharge is more effectively removed during cleaning. This leads to increased comfort for the user.

In another embodiment of the invention the coupling assembly, the third coupling element is a lock ring. One advantage of this embodiment is that the lock ring can be adapted to be manipulated by the user.

In a preferred embodiment the body-side coupling part comprises the first coupling element.

In a particularly preferred embodiment the body-side coupling part comprises the second coupling element. One advantage of this particular embodiment is that the second coupling element is often more expensive to manufacture than the first coupling element. When the reusable body-side coupling part comprises the second coupling element, it is possible to reuse the second coupling element as well, which will result in an overall cost advantage.

In one embodiment of the invention the body-side coupling part comprises the third coupling element.

In a particularly preferred embodiment the body-side coupling part comprises the second and third coupling element. The third coupling element can be provided as a lock ring mounted on the second coupling element to be movable between a locking position and an unlocking position. A particular advantage of this embodiment is that the user of the ostomy bag, and thus the coupling assembly, does not have to orientate the second and the third coupling element in relation to each other when coupling the coupling assembly, as the second and third coupling element are already coupled correctly prior to delivery. A further advantage of this embodiment is that a substantial part of the coupling assembly, namely the second and third coupling element, is mounted on the body-side coupling part, which can be reused. Thus, the overall cost can be reduced, since substantial parts are placed on the reusable body-side coupling part, leaving only the first coupling part to be disposed off when the ostomy bag is replaced.

One embodiment of the invention relates to a coupling assembly where the third coupling element is a plastic part. In a preferred embodiment the third coupling element is a plastic part with at least two components. Since different parts of the third coupling element can have different functions, e.g. one part is to be manipulated by the user and another part is a part in the coupling of the coupling assembly, different characteristic and thereby different qualities of plastic may be desirable. Thus, for providing the third coupling element with the desired properties, it can be provided with more than one component, e.g. a relatively softer plastic material for the part of the third coupling element, which is to be manipulated by the user, and a relatively more rigid plastic material for the part of the third coupling element, which is to engage in the coupling assembly.

One embodiment of the invention relates to a coupling assembly, where the first coupling element is provided with additional sealing means. Providing the first coupling element with additional sealing means can minimize the risk of leakage, which is a major concern for many users. Additional sealing means contributes to a safe and tight coupling assembly, leading to an increase in comfort for the user.

Another embodiment of the invention relates to a coupling assembly, where the second coupling element is provided with additional sealing means. Providing the first coupling element with additional sealing means can minimize the risk of leakage, which is a major concern for many users. Additional sealing means contributes to a safe and tight coupling assembly, leading to an increase in comfort for the user.

In one embodiment of the invention the sealing means is provided as a sealing lip.

In another embodiment of the invention the sealing means is provided as a sealing rib.

One embodiment of the invention relates to a coupling assembly, wherein the first coupling element on a proximal surface is provided with a U-shaped groove seen in cross-section. The U-shaped groove is adapted to receive the second coupling element when coupling the coupling assembly. However, it will be appreciated by the skilled person that the groove may have many different shapes, e.g. a V-shape or it may be provided with integrated sealing means to minimize leakage.

In a preferred embodiment of the invention the second coupling element and the third coupling element are provided with first and second guiding means respectively, the first and second guiding means being in the form of a thread.

The second coupling element and the third coupling element engage each other via a thread. When the third coupling element is rotated, the thread causes a displacement of the third coupling element in an axial direction away from a proximal surface of the second coupling element leading a distal and/or outer surface of the second coupling element into abutment against the first coupling element.

It shall be understood that depending on the desired performance of the coupling assembly the thread may in different embodiments have different numbers of tracks and that within the scope of the invention the pitch may also be changed between embodiments. Thus, it is possible to predetermine the linear axial motion relative to the rotary motion, which the user exerts on the third coupling element.

In a preferred embodiment the first and second guiding means is in the form a thread, and the body-side coupling part comprises the second and third coupling element. As known from threaded coupling assemblies, e.g. U.S. Pat. No. 4,846, 798, the coupling elements, when positioned in a concentric position, need to be angularly orientated in relation to each other as there is only a limited number of positions where the initial engagement between two threaded coupling parts can take place. When the body-side coupling part comprises both the second and third coupling element, the coupling between the second and third coupling element can be done prior to delivery to the user. Thus, the angular orientation needed between the second and third coupling element is eliminated for the user. This makes the coupling of the coupling assembly easy, as the user then only has to couple the first coupling element with the already assembled second and third coupling element. This latter coupling does not include any angular orientation and is thus simple to perform by the user.

In order to prevent unintentional uncoupling between the coupling elements there may in the threaded parts be provided a recess in one part, e.g. in the second coupling element, and a protrusion in the other part, e.g. the third coupling element, wherein said recess is adapted to receive said protrusion. This also allows for a snap-lock when the elements are properly coupled and the third element is properly rotated in order to lock the second engagement area with the first engagement area. Such snap-lock will indicate to a user that the ostomy coupling arrangements has been correctly and fully coupled with each other.

FIGURES

All figures show a first embodiment of the invention. Not all described features are visible in each figure, but can be seen in other figures.

FIG. 1 shows an exploded view of a first embodiment of the coupling assembly according to the invention, FIG. 2 shows an exploded view of the first embodiment of the coupling assembly in FIG. 1 from another view, FIG. 3 shows a perspective sectional view of the first coupling element, which is to be attached to the ostomy bag, of the coupling assembly in FIG. 1, FIG. 4 shows a perspective view of the third coupling element, in the form of a lock ring, of the coupling assembly in FIG. 1, FIG. 5 shows a perspective sectional view of the second coupling element of the coupling assembly in FIG. 1, FIG. 6 shows an exploded view of the first embodiment of the coupling assembly in FIG. 1 in an unlocking position, FIG. 7 shows a perspective view of the first embodiment of the coupling assembly in FIG. 1 in a locking position, FIGS. 8a, 8b, and 8c show respectively a front view, a sectional view along line II-II in FIG. 8a, and a partial, enlarged sectional view along the line II-II in FIG. 8a of the coupling assembly in FIG. 1, all in which the coupling assembly is in an unlocking position, FIGS. 9a, 9b, and 9c show respectively a front view, a sectional view along line III-III in FIG. 9a, and a partial, enlarged sectional view along the line III-III in FIG. 9a of the coupling assembly in FIG. 1, all in which the coupling assembly is in a locking position, FIG. 10 shows the operation of the first embodiment according to the invention in FIG. 1, and FIG. 11 shows the operation of a second embodiment according to the invention.

DETAILED DISCLOSURE

FIGS. 1 and 2 show a first embodiment of the invention in an exploded view. The coupling assembly 1 comprises a first coupling element 2, a second coupling element 3 and a third coupling element 4. The first coupling element 2 is adapted to be attached to an ostomy bag (not shown), and the second coupling element 3 is adapted to be attached to a base plate (not shown). The third coupling element 4 is provided to help and secure the engagement and thus the coupling of the first and the second coupling elements 2, 3. Thus, when coupled, the coupling assembly 1 will couple the base plate and ostomy bag together, and the coupling assembly 1 will thus be arranged between the plate and the bag.

In the following it should be understood that each element of the coupling assembly can be viewed as being divided into a number of different parts as will be understood in the following. The parts have an axial extent, which extends along the axis I-I. The axial extent is defined by a proximal surface of the part and a distal surface of the part. The proximal surface of the part is the surface that faces the base plate and the distal surface of the part is the surface that faces the ostomy bag.

Furthermore, the elements also have a radial extent, being an extent transverse to the axis I-I, defined as being between an inner surface of the part and an outer surface of the part. The inner surface faces inwards towards the axis I-I, and the outer surface faces outwards away from the axis I-I.

In FIG. 3 the first coupling element 2 is shown in a sectional view. The first coupling element 2 has a proximal surface which is provided with a U-shaped groove 6 seen in cross section. The U-shaped groove 6 is provided to accommodate the second coupling element 3 and comprises a first engagement area 7 in the U-shaped groove 6, which first engagement area 7 is to come into abutment with at least a part of the second coupling element 3 during the locking of the coupling assembly 1. The first coupling element 2 has a distal surface provided with a first attachment area 8, where the first coupling element 2 is to be attached to the ostomy bag in any suitable manner, e.g. by means of welding, laser welding, gluing etc. In order to easily remove the ostomy bag and thus the attached first coupling element 2 from the base plate, and thus the second and third coupling elements 3, 4, after use, there is provided a flap 14 on the outer surface of the first coupling element 2, which flap 14 is easy to grab with the fingers.

In one embodiment the first coupling element 2 is provided with additional sealing means in the form of a rib or lip at the inner surface of the U-shaped groove 6 in order to provide extra safety against leakage.

FIG. 4 shows the third coupling element 4 in one embodiment, where it is provided as a two-component plastic part comprising a gripping part 10 and the locking member in form of a threaded part 5. The two components, i.e. in this case the gripping part 10 and the threaded part 5, of the third coupling element 4 can be joined by welding, laser welding or gluing or in any other suitable manner, or the two components of third coupling element 4 can be moulded in one piece by injection moulding. On the inner surface, the third coupling element 4 is provided with a first thread 9 which is adapted to engage a corresponding thread on the second coupling part 3. On the outer surface, the third coupling element 4 is provided with a gripping part 10 designed to be easily and comfortably handled by the user in a rotational movement when he/she wishes to lock or unlock the coupling assembly 1.

Preferably, the gripping part 10 can be provided in a softer material than the first thread 9 in order to provide a comfortable and easy grip of the third coupling element 4. This material could for example be EVA (Ethylene-vinyl-acetate) or TPE (Thermo-plastic-elastomers). The material of the first thread 9 could for example be PP (Polypropylene) or ABS (acryinitril-butadiene-styrene-copolymer).

The gripping part can be provided in many different forms and is not limited to the example which is described above. For example the gripping part can be provided comprising finger-sized notches for easy gripping and handling.

FIG. 5 shows the second coupling element 3 of the coupling assembly 1. The second coupling element 3 has a proximal surface with a second attachment area 11 which is to be attached to the base plate by means of welding, laser welding, gluing or in any other suitable manner. The second coupling element 3 comprises an axially extending inner wall 16 and an axially extending outer wall 17 with an connection part 18 provided between the inner wall 16 and the outer wall 17. The outer surface of the inner wall 16 is provided with a second thread 12 which is adapted to accommodate the first thread 9 of the third coupling element 4. In a preferred embodiment, the first and the second thread 9, 12 is designed with a thread lead so that the third coupling element 4 has to be rotated about 90° in relation to the second coupling element 3 in order to reach the locking position of the coupling assembly 1 from the unlocking position and vice versa.

The outer surface of the outer wall 17 comprises a second engagement area 13 which is adapted to come into abutment with the first engagement area 7 of the first coupling element 2 in a locking position. In this embodiment the outer surface of the outer wall 17 is designed as a uniform, curved surface, but it can be designed in several ways to provide its function, namely to provide sealing between the first coupling element 2 and the second coupling element 3. For example the second coupling element 3 can be provided with additional sealing means in the form of a rib or lip at either the outer surface of the outer wall 17, the distal surface of the connection part 18 or the inner surface of the inner wall 16 in order to provide extra safety against leakage.

The coupling assembly 1 is coupled as shown in FIGS. 6 and 7. When delivered from the manufacturer the third coupling element 4 is mounted on the second coupling element 3, which in turn is attached to a base plate 15. The U-shaped groove 6 (as seen in FIG. 3) of the first coupling element 2 is placed over the second coupling element 3 as indicated by the arrow A in FIG. 6. The user then rotates the third coupling element 4, as indicated by the arrow B in FIG. 7, to cause an axial displacement of the third coupling element 4 in relation to the second coupling element 3 so that the first engagement area 7 of the first coupling element 2 comes into abutment with the second engagement area 13 of the second coupling element 3. The third coupling element 4 forces the second coupling element 3 and thereby the second engagement area 13 to press against the first engagement area 7 of the first coupling element 2.

FIG. 7 shows the coupling assembly 1 in its locking position. The unlocking of the coupling assembly 1 is performed by rotating the third coupling element 4 in the opposite direction in relation to locking. When the third coupling element 4 has been rotated about 90° to the unlocking position, the first coupling element 2 and thus the attached ostomy bag (not shown) can be removed.

In one embodiment of the invention the second coupling part 3 is dimensioned in such a way that the second coupling part 3 fits comfortably into the U-shaped groove 6 of the first coupling element 2 without applying any noticeable force in order to place the second coupling part 3 in the U-shaped groove 6. In this embodiment the outer diameter of the second coupling element 3 is somewhat smaller than the diameter of the first coupling element 2 measured from the outermost points of the U-shaped groove 6. When the third coupling element 4 subsequently is rotated, the third coupling element 4 forces the second engagement area 13 of the second coupling element 3 outwards in a radial direction leading the second engagement area 13 into abutment with the first engagement area 7. This way the function of the third coupling element 4 is to force the second coupling element 3 into abutment with the first coupling element 2 and keep the first and second coupling elements 2, 3 in abutment in a locking position.

In another embodiment of the invention the second coupling part 3 is dimensioned in such a way that the second coupling part 3 has to be pressed into the U-shaped groove 6 of the first coupling element 2 with some force like in a well-known snap configuration. In this embodiment the outer diameter of the second coupling element 3 is substantially similar to the diameter of the first coupling element 2 measured from the outermost points of the U-shaped groove 6. After the second coupling part 3 has been snapped into the U-shaped groove 6 of the first coupling element 2, the first coupling element 2 and the second coupling element 3 are in engagement. When the third coupling element 4 subsequently is rotated, the third coupling element 4 secures the engagement between the first and the second coupling element 2, 3 further by pressing the distal surface of the second coupling element 3 outwards in a radial direction. This way the function of the third coupling element 4 is to secure the second coupling element 3 in abutment with the first coupling element 2 and thus keep the first and second coupling elements 2, 3 in a locking position. One advantage of this particular embodiment is that the second coupling element 3 is securely retained in the U-shaped groove 6 of the first coupling element 2 after the unlocking rotational movement of the third coupling element 4 after use. The first coupling element 2 and thus the attached ostomy bag can subsequently be removed by pulling the flap 14 of the first coupling element. This snap configuration thus impedes unintentional dropping of the ostomy bag during the locking and unlocking of the coupling assembly 1. In addition, the coupling assembly becomes easier to handle with only one hand, as it is not necessary to hold the ostomy bag and rotate the third coupling element 4 at the same time neither in the locking nor the unlocking situation. This may for example be provided by molding the second coupling element 3 in its engagement position, wherein the second engagement area 13 of the second coupling part engages with the first engagement area 7 of the first coupling element 2. Thus, the second coupling element will be biased towards it engagement position when deformed.

In one embodiment the first thread 9 or the second thread 12 is provided with a stop or the like in the thread in order to provide a click feature to indicate to the user that the locking of the coupling assembly 1 is complete.

In another embodiment the first thread 9 or the second thread 12 is provided with a stop or the like in the thread in order to provide a click feature to indicate to the user that the unlocking of the coupling assembly 1 is complete so that the ostomy bag can be removed.

FIG. 8a shows the assembled coupling assembly 1 in a front view. The coupling assembly 1 is in the unlocking position.

FIG. 8b shows the coupling assembly 1 seen in section along line II-II in FIG. 8a.

Figure 3:
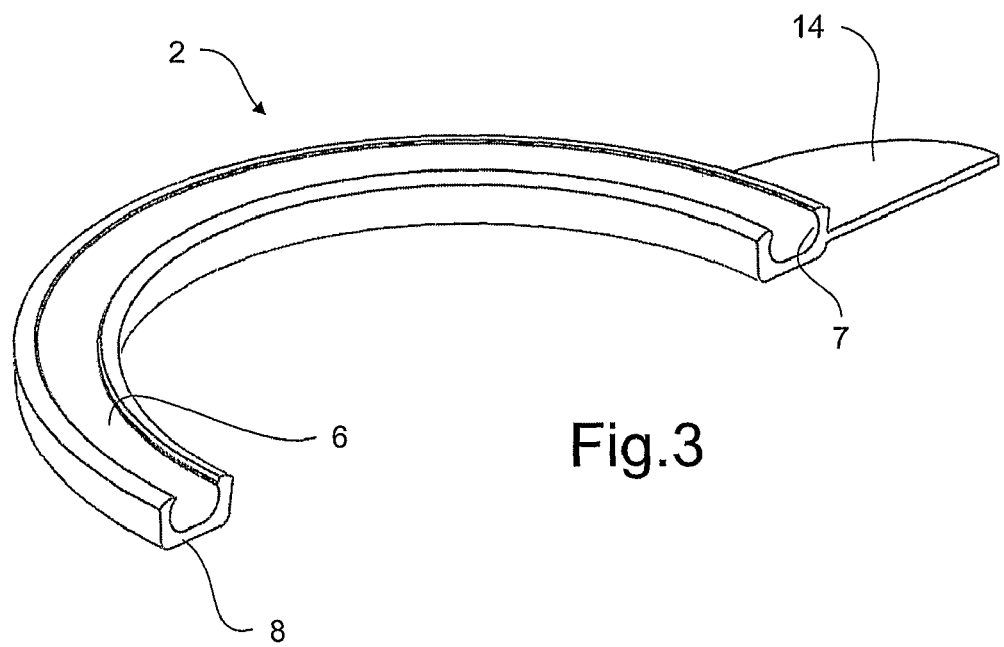
Figure 4:
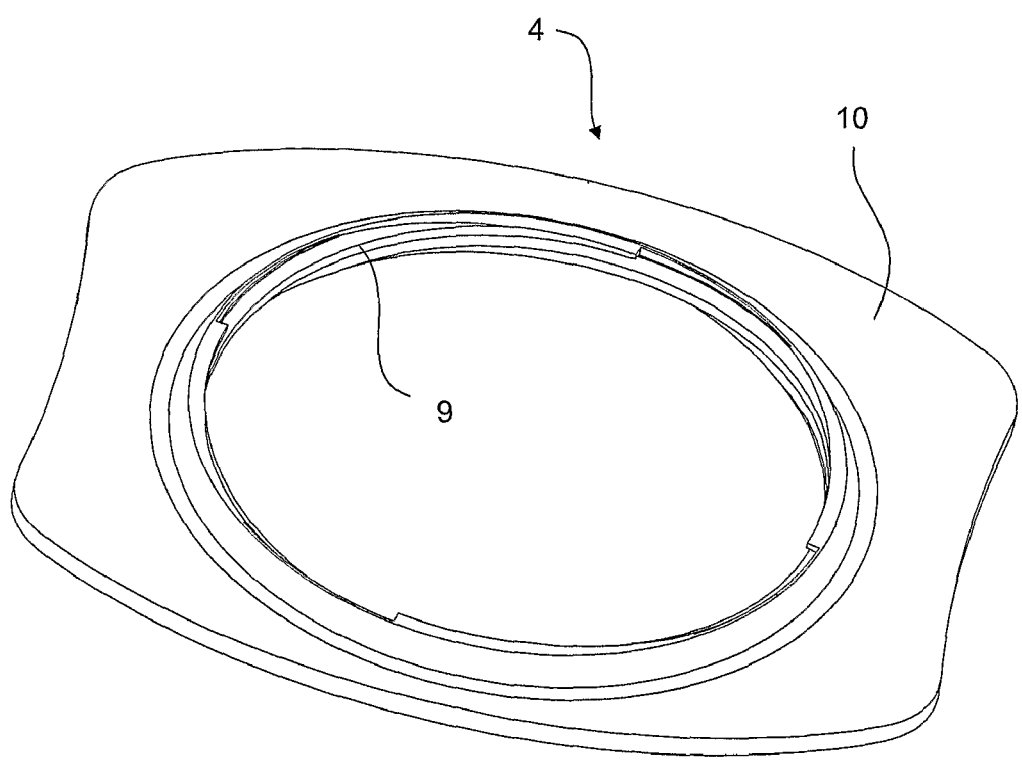
Figure 5:
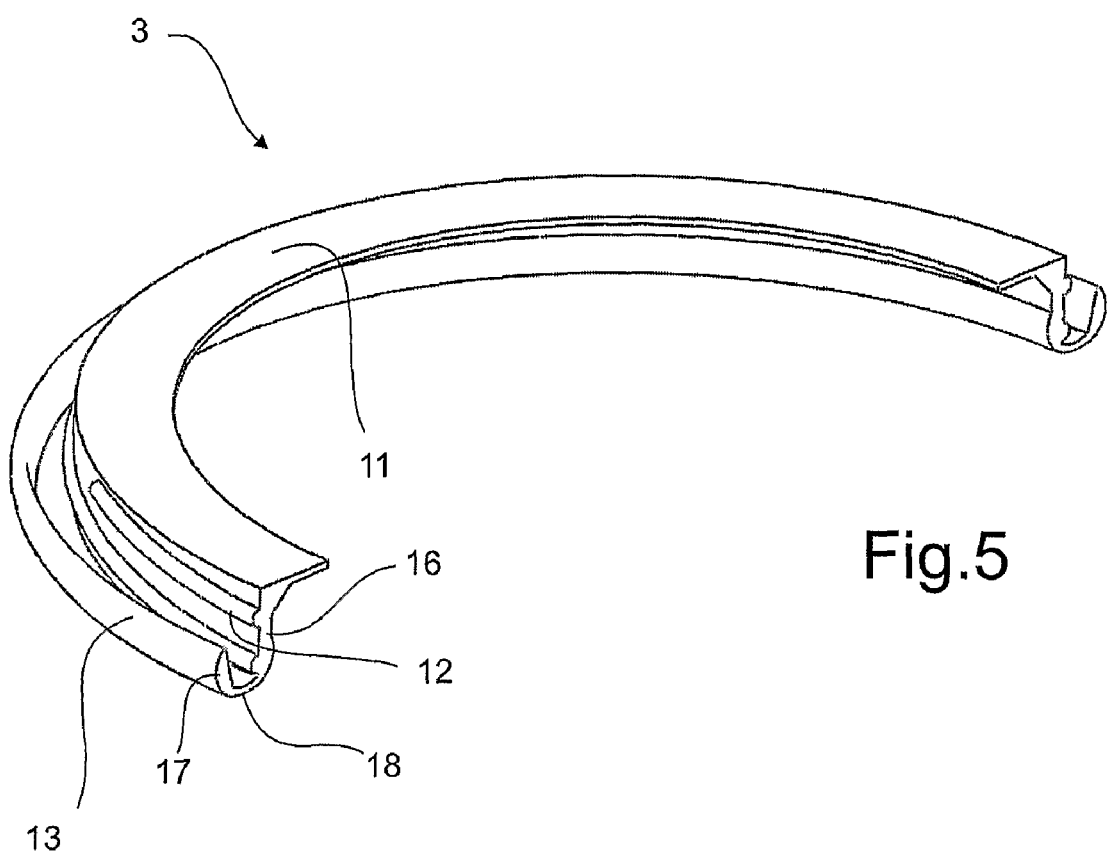
Figure 6:
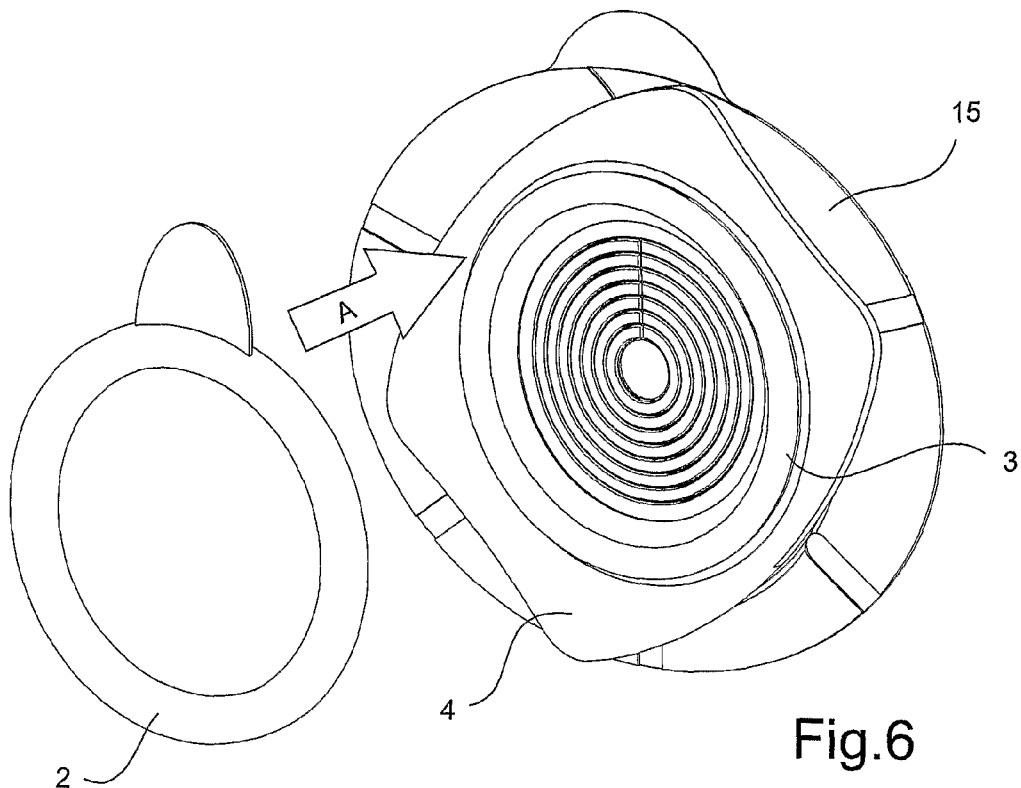
Figure 7:
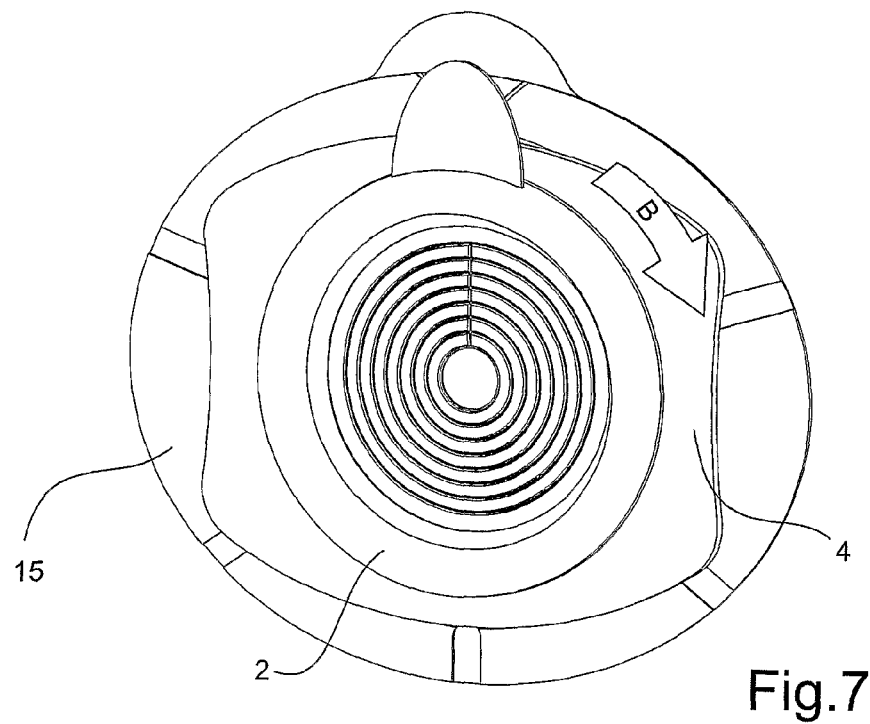

In order to better illustrate parts of the assembled coupling assembly 1 parts of section II-II of FIG. 8b have been enlarged in FIG. 8c. The third coupling element 4 is shown as a two-component plastic part with the first thread 9 and the gripping part 10. The third coupling element 4 is in a neutral position, and thus the second coupling element 3 is not manipulated into abutment with the first coupling element 2.

The relations between the first engagement area 7 and the second engagement area 13 are defined by radii all of which is related to the axis I-I (seen in FIG. 8b). As best seen in FIG. 8c, the first engagement area 7 extends between the first inner radius a and the first outer radius b. The second engagement area 11 extends between the second inner radius c and the second outer radius d. The second outer radius d is smaller than the first inner radius a, and thus the second engagement area 13 is in the disengagement position in FIG. 8c.

FIG. 9a shows the assembled coupling assembly 1 in a front view. The coupling assembly 1 is in the locking position.

FIG. 9b shows the coupling assembly 1 seen in section along line III-III in FIG. 9a.

In order to better illustrate parts of the assembled coupling assembly 1 parts of section III-III of FIG. 9b have been enlarged in FIG. 9c.

In FIG. 9c the relations between the first engagement area 7 and the second engagement area 13 can also be seen defined by the radii a, b, c, d. In FIG. 9c, the second engagement area is in the engagement position, the second outer radius d being larger than the first inner radius a.

The coupling assembly 1 is illustrated around a mutual axis I-I which defines the axial and radial extent of the coupling assembly 1. Although the coupling assembly 1 in the illustrated embodiment is circularly formed around the axis I-I, other embodiments within the scope of the invention may have other shapes and may be symmetrically or unevenly provided around a corresponding axis.

Figure 10:
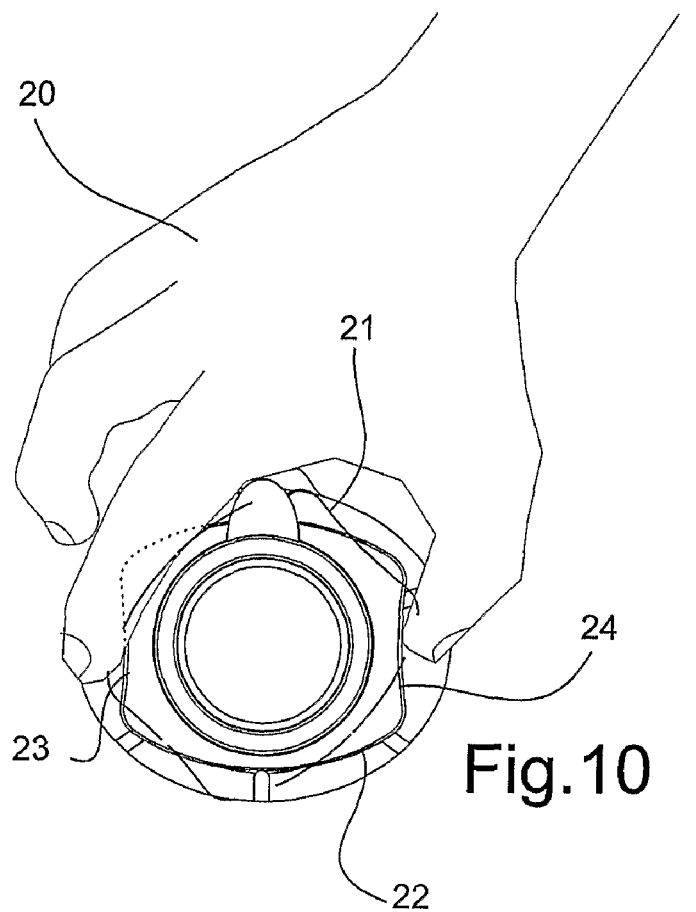

FIG. 10 shows how a user can manipulate the locking ring 4 in the first embodiment of the coupling assembly in which a user 20 moves the locking ring 45 degrees clockwise from its unlocked position 21 to its locked position 22.

In one embodiment the first thread 9 of the locking ring 4 and the surrounding area will be formed of a relative stiff material, which prevents that the thread bends and thereby hampers the operation of the locking ring. However, in order to provide easy handling the locking ring is provided with two tabs 23, 24 which is formed of a soft material which increases friction between the tabs and the skin of the users fingers. Advantageously two-component injection molding may provide such a locking ring consisting of two materials.

Figure 11:
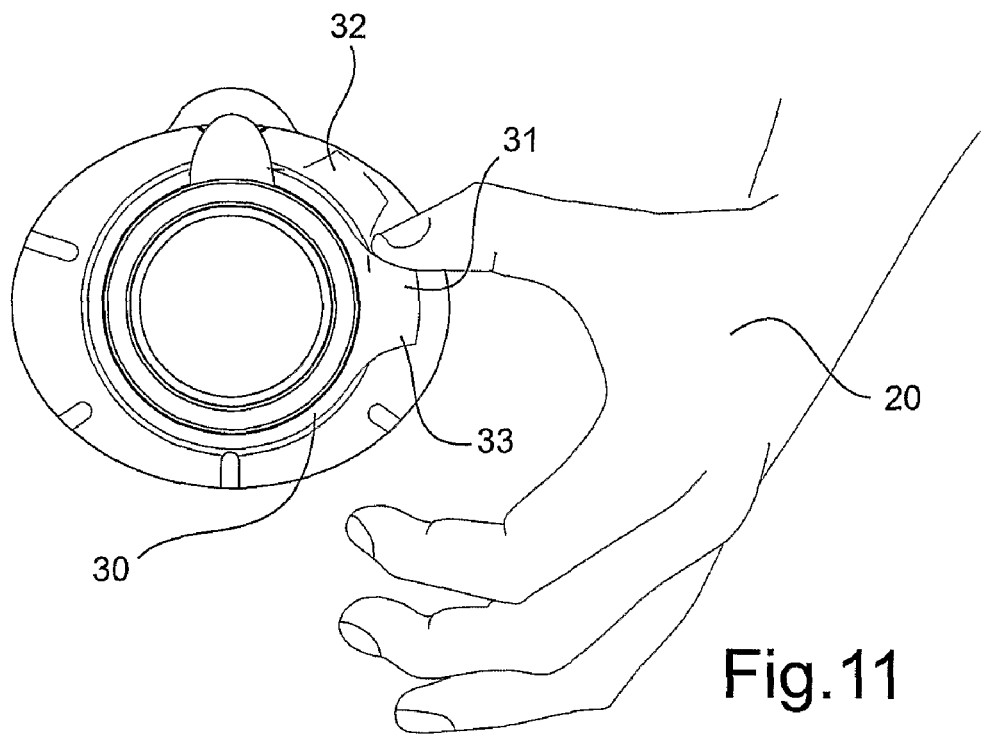

A second embodiment of the locking ring 30 is shown in FIG. 11. In this embodiment the locking ring 30 is only provided with one tab 31, which allows the user to operate the locking ring with only one finger, e.g. the thumb which might be preferable for users who suffer from reduced use of their limbs.

As in FIG. 10 the second embodiment of the locking ring 30 is also moved from a unlocked position 32 to a locking position 33 by rotating the locking ring 45 degrees clockwise.

The tab 31 is like described above formed of a soft high friction material, while the thread is formed of a stiffer material, which provides small friction when used in a threaded coupling.

The invention claimed is:

1. An ostomy device coupling assembly comprising a first, second and third coupling element for coupling a first and second part to each other in an axial direction, wherein
   the first coupling element comprises a first engagement area, extending between a first inner radius and a first outer radius,
   the second coupling element comprises a second engagement area extending between a second inner radius and a second outer radius,
   the third coupling element comprising a locking member and being axially displaceable in relation to the second coupling element between a locking position and an unlocking position,
   and wherein the locking member is disposed between the second inner radius and the second outer radius of the second engagement area, the locking member radially displaceable to an engagement position in which the locking member expands the second outer radius to a size larger than the first inner radius and radially displaceable to a disengagement position in which the locking member allows the second outer radius to retract to a size smaller than the first inner radius.

2. A coupling assembly according to claim 1, wherein the coupling assembly is a coupling assembly for a two-piece ostomy bag including a body-side coupling part and a bag-side coupling part.

3. A coupling assembly according to claim 1, wherein the third coupling element is a lock ring.

4. A coupling assembly according to claim 2, wherein the body-side coupling part comprises the first coupling element.

5. A coupling assembly according to claim 2, wherein the body-side coupling part comprises the second coupling element.

6. A coupling assembly according to claim 2, wherein the body-side coupling part comprises the third coupling element.

7. A coupling assembly according to claim 1, where the third coupling element is a plastic part.

8. A coupling assembly according to claim 7, where the third coupling element is a plastic part with at least two components.

9. A coupling assembly according to claim 1, wherein the first coupling element is provided with a seal.

10. A coupling assembly according to claim 9, wherein the seal is a sealing lip.

11. A coupling assembly according to claim 9, wherein the seal is a sealing rib.

12. A coupling assembly according to claim 1, wherein the second coupling element is provided with a seal.

13. A coupling assembly according to claim 1, wherein the first engagement area of the first coupling element is a U-shaped groove provided on a proximal surface.

14. A coupling assembly according to claim 1, wherein the second coupling element includes a guide thread that mates with a guide thread of the third coupling element.

* * * * *